United States Patent
Lee et al.

(10) Patent No.: US 10,821,085 B2
(45) Date of Patent: *Nov. 3, 2020

(54) WIPE COATED WITH A BOTANICAL COMPOSITION HAVING ANTIMICROBIAL PROPERTIES

(75) Inventors: Jaehong Lee, Gyeonggi-do (KR); Vasily A. Topolkaraev, Appleton, WI (US); Neil T. Scholl, Neenah, WI (US); YoungSook Kim, Gyeonggi-do (KR); David W. Koenig, Menasha, WI (US); James H. Wang, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 664 days.

This patent is subject to a terminal disclaimer.

(21) Appl. No.: 12/961,611

(22) Filed: Dec. 7, 2010

(65) Prior Publication Data

US 2012/0141569 A1    Jun. 7, 2012

(51) Int. Cl.
| *A01N 25/34* | (2006.01) |
| *A01P 1/00* | (2006.01) |
| *B05D 3/02* | (2006.01) |
| *A61K 31/05* | (2006.01) |
| *A01N 65/00* | (2009.01) |
| *A01N 31/08* | (2006.01) |
| *D06N 3/12* | (2006.01) |
| *D06N 3/00* | (2006.01) |
| *A61F 13/36* | (2006.01) |

(52) U.S. Cl.
CPC .............. *A61K 31/05* (2013.01); *A01N 31/08* (2013.01); *A01N 65/00* (2013.01); *D06N 3/0059* (2013.01); *D06N 3/126* (2013.01); *D06N 3/128* (2013.01); *A61F 13/36* (2013.01); *D06N 2209/1671* (2013.01); *D06N 2211/08* (2013.01); *Y02A 50/473* (2018.01)

(58) Field of Classification Search
CPC ...................................................... A01N 25/34
See application file for complete search history.

(56) References Cited

U.S. PATENT DOCUMENTS

| 3,354,506 A | 11/1967 | Raley |
| 3,494,821 A | 2/1970 | Evans |
| 3,650,649 A | 3/1972 | Schippers |
| 3,801,429 A | 4/1974 | Schrenk et al. |
| 3,973,695 A | 8/1976 | Ames |
| 4,100,324 A | 7/1978 | Anderson et al. |
| 4,144,370 A | 3/1979 | Boulton |
| 4,652,441 A | 3/1987 | Okada et al. |
| 4,690,825 A | 9/1987 | Won |
| 4,695,450 A | 9/1987 | Bauer et al. |
| 4,820,435 A | 4/1989 | Zafiroglu |
| 5,023,080 A | 6/1991 | Gupta |
| 5,057,361 A | 10/1991 | Sayovitz et al. |
| 5,179,164 A | 1/1993 | Lausberg et al. |
| 5,240,764 A | 8/1993 | Haid et al. |
| 5,284,703 A | 2/1994 | Everhart et al. |
| 5,320,669 A | 6/1994 | Lim et al. |
| 5,330,768 A | 7/1994 | Park et al. |
| 5,350,624 A | 9/1994 | Georger et al. |
| 5,354,726 A | 10/1994 | Narayanan et al. |
| 5,395,055 A | 3/1995 | Shutov et al. |
| 5,397,834 A | 3/1995 | Jane et al. |
| 5,421,898 A | 6/1995 | Cavanagh |
| 5,523,293 A | 6/1996 | Jane et al. |
| 5,589,195 A | 12/1996 | Potter |
| 5,665,428 A | 9/1997 | Cha et al. |
| 5,687,875 A | 11/1997 | Watts et al. |
| 5,702,717 A | 12/1997 | Cha et al. |
| 5,723,588 A | 3/1998 | Donofrio et al. |
| 5,735,588 A | 4/1998 | Dittman et al. |

(Continued)

FOREIGN PATENT DOCUMENTS

| EP | 0388718 A2 | 9/1990 |
| EP | 0388718 A3 | 9/1990 |

(Continued)

OTHER PUBLICATIONS

Article—Auvergne et al., "Reactivity of Wheat Gluten Protein during Mechanical Mixing: Radical and Nucleophilic Reactions for the Addition of Molecules on Sulfur," *Biomacromolecules*, vol. 9, No. 2, 2008, pp. 664-671.

Article—Camire, Mary Ellen, "Protein Functionality Modification by Extrusion Cooking," *JAOCS*, vol. 68, No. 3, Mar. 1991, pp. 200-205 (Presented at the 81st AOCS Annual Meeting, Baltimore, 1990).

Article—Hu et al., "Evaluation of the environmental fate of thymol and phenethyl Propionate in the laboratory," *Pest Management Science*, vol. 64, Issue 7, Jul. 2008, pp. 775-779.

Article—Kurniawan et al., "Chemical Modification of Wheat Protein-Based Natural Polymers: Grafting and Cross-Linking Reactions with Poly(ethylene oxide) Diglycidyl Ether and Ethyl Diamine," *Biomacromolecules*, vol. 8, No. 9, 2007, pp. 2909-2915.

(Continued)

*Primary Examiner* — Kyle A Purdy
(74) *Attorney, Agent, or Firm* — Dority & Manning, P.A.

(57) ABSTRACT

A wipe containing a fibrous web on which is coated an antimicrobial composition is provided. The composition includes a botanical oil derived from a plant (e.g., thymol, carvacrol, etc.). Because the oil is volatile and tends to evaporate and lose efficacy prior to use, a protein is also employed to enhance the composition's long term stability and antimicrobial efficacy. The protein tends to form a substantially continuous film when coated onto the fibrous web. Because such proteins are typically stiff and brittle, a continuous film would restrict the ability of the fibers to move and bend, reducing web flexibility and drape. Thus, it is typically desired that the antimicrobial composition form a discontinuous coating on the web. In this regard, the present inventors have surprisingly discovered that the addition of an organopolysiloxane can help achieve a discontinuous coating without adversely impacting the ability of the protein to stabilize the oil.

28 Claims, 3 Drawing Sheets

(56) References Cited

U.S. PATENT DOCUMENTS

| | | |
|---|---|---|
| 5,785,179 A | 7/1998 | Buczwinski et al. |
| 5,871,872 A | 2/1999 | Matijevic et al. |
| 5,882,702 A | 3/1999 | Abdel-Malik et al. |
| 5,919,471 A | 7/1999 | Saferstein et al. |
| 5,928,661 A | 7/1999 | Fujita et al. |
| 5,964,351 A | 10/1999 | Zander |
| 6,030,331 A | 2/2000 | Zander |
| 6,090,925 A | 7/2000 | Woiszwillo et al. |
| 6,121,165 A | 9/2000 | Mackey et al. |
| 6,133,166 A | 10/2000 | Nissing et al. |
| 6,158,614 A | 12/2000 | Haines et al. |
| 6,269,969 B1 | 8/2001 | Huang et al. |
| 6,269,970 B1 | 8/2001 | Huang et al. |
| 6,270,878 B1 | 8/2001 | Wegele et al. |
| 6,273,359 B1 | 8/2001 | Newman et al. |
| 6,315,864 B2 | 11/2001 | Anderson et al. |
| 6,482,423 B1* | 11/2002 | Beerse et al. ............... 424/404 |
| 6,523,690 B1 | 2/2003 | Buck et al. |
| 6,568,625 B2 | 5/2003 | Faulks et al. |
| 6,589,549 B2 | 7/2003 | Shih et al. |
| 6,719,995 B2 | 4/2004 | Rajaiah et al. |
| 6,766,919 B2 | 7/2004 | Huang et al. |
| 6,770,433 B2 | 8/2004 | Hioki |
| 6,773,718 B2* | 8/2004 | Seth et al. ............... 424/443 |
| 6,806,213 B2 | 10/2004 | Brooks |
| 6,806,353 B2 | 10/2004 | Zhang et al. |
| 6,824,734 B2 | 11/2004 | Boggs et al. |
| 6,989,149 B2 | 1/2006 | Glenn, Jr. et al. |
| 7,127,771 B2 | 10/2006 | McDevitt et al. |
| 7,250,152 B2 | 7/2007 | Gentile et al. |
| 7,338,927 B2 | 3/2008 | Shapiro |
| 7,462,348 B2 | 12/2008 | Gruenbacher et al. |
| 7,560,422 B2 | 7/2009 | Shapiro |
| 7,605,096 B2 | 10/2009 | Tomarchio et al. |
| 7,612,029 B2 | 11/2009 | Foland et al. |
| 7,614,812 B2 | 11/2009 | Reddy et al. |
| 7,662,409 B2 | 2/2010 | Masters |
| 7,803,413 B2 | 9/2010 | van Lengerich et al. |
| 7,803,414 B2 | 9/2010 | Van Lengerich et al. |
| 2003/0031722 A1 | 2/2003 | Cao et al. |
| 2003/0082219 A1 | 5/2003 | Warren et al. |
| 2003/0105207 A1 | 6/2003 | Kleyer et al. |
| 2003/0135172 A1 | 7/2003 | Whitmore et al. |
| 2003/0194416 A1* | 10/2003 | Shefer ............... A61K 8/732 424/401 |
| 2004/0018241 A1 | 1/2004 | Houze et al. |
| 2004/0026289 A1 | 2/2004 | Halkyard |
| 2004/0037870 A9 | 2/2004 | Fotinos |
| 2004/0234609 A1 | 11/2004 | Collier et al. |
| 2004/0241236 A1* | 12/2004 | Li ............... A23G 1/54 424/471 |
| 2004/0255408 A1 | 12/2004 | Norton et al. |
| 2005/0048121 A1 | 3/2005 | East et al. |
| 2005/0089548 A1* | 4/2005 | Virgalitto ............ A23L 1/22016 424/440 |
| 2005/0158369 A1 | 7/2005 | Dorschner et al. |
| 2005/0214349 A1 | 9/2005 | Nie et al. |
| 2005/0238591 A1 | 10/2005 | Sagel et al. |
| 2005/0245162 A1 | 11/2005 | McCormack et al. |
| 2006/0036223 A1* | 2/2006 | Baldwin et al. ............. 604/360 |
| 2006/0062832 A1 | 3/2006 | Lopes |
| 2006/0128248 A1 | 6/2006 | Ellis |
| 2007/0042184 A1* | 2/2007 | Coyne ............... A21D 2/00 428/402.2 |
| 2007/0224261 A1 | 9/2007 | Draper |
| 2007/0254035 A1 | 11/2007 | Hao et al. |
| 2007/0256247 A1 | 11/2007 | Privitera et al. |
| 2007/0269567 A1 | 11/2007 | McMindes et al. |
| 2008/0160084 A1 | 7/2008 | Huynh et al. |
| 2008/0200359 A1 | 8/2008 | Smets et al. |
| 2008/0207481 A1 | 8/2008 | Meine et al. |
| 2008/0221003 A1 | 9/2008 | Meine et al. |
| 2009/0136555 A1 | 5/2009 | Crowley et al. |
| 2009/0175806 A1 | 7/2009 | Modak et al. |
| 2009/0186096 A1 | 7/2009 | Kritzman et al. |
| 2009/0196909 A1 | 8/2009 | Cooper et al. |
| 2009/0226530 A1 | 9/2009 | Lassner et al. |
| 2009/0232905 A1 | 9/2009 | Weiss et al. |
| 2009/0246240 A1* | 10/2009 | Holmberg ............... 424/409 |
| 2009/0286437 A1 | 11/2009 | Cunningham et al. |
| 2009/0297664 A1 | 12/2009 | Forte et al. |
| 2010/0034907 A1 | 2/2010 | Daigle et al. |
| 2010/0065445 A1 | 3/2010 | Stevenson |
| 2010/0101605 A1 | 4/2010 | Saint Victor |
| 2010/0136201 A1 | 6/2010 | Bigeard et al. |
| 2010/0144584 A1 | 6/2010 | Saint Victor |
| 2010/0234517 A1 | 9/2010 | Plantenberg et al. |
| 2010/0240724 A1 | 9/2010 | Chang et al. |
| 2010/0240799 A1 | 9/2010 | Hofmann et al. |
| 2010/0247371 A1 | 9/2010 | Farrugia et al. |
| 2010/0272831 A1 | 10/2010 | Lagaron Cabello et al. |
| 2011/0086084 A1 | 4/2011 | Koenig et al. |
| 2011/0086085 A1 | 4/2011 | Wenzel et al. |
| 2011/0150955 A1 | 6/2011 | Klingman |

FOREIGN PATENT DOCUMENTS

| | | |
|---|---|---|
| EP | 0504387 B1 | 7/1995 |
| EP | 0863942 B1 | 9/1998 |
| EP | 1004703 A1 | 5/2000 |
| EP | 1023863 A1 | 8/2000 |
| EP | 1059032 A1 | 12/2000 |
| EP | 1059378 A1 | 12/2000 |
| EP | 1275370 A1 | 1/2003 |
| EP | 1275371 A1 | 1/2003 |
| EP | 1624013 A1 | 2/2006 |
| EP | 1757261 A2 | 2/2007 |
| EP | 1757261 A3 | 2/2007 |
| EP | 1867317 A2 | 12/2007 |
| EP | 1867317 A3 | 12/2007 |
| FR | 2900940 A1 | 11/2007 |
| GB | 2444112 A | 5/2008 |
| WO | WO 9003784 A1 | 4/1990 |
| WO | WO 9205708 A1 | 4/1992 |
| WO | WO 0151557 A1 | 7/2001 |
| WO | WO 02074430 A1 | 9/2002 |
| WO | WO 06000032 A1 | 1/2006 |
| WO | WO 07135273 A2 | 11/2007 |
| WO | WO 07135273 A3 | 11/2007 |
| WO | WO 08030969 A2 | 3/2008 |
| WO | WO 08030969 A3 | 3/2008 |
| WO | WO 08063088 A1 | 5/2008 |
| WO | WO 08063088 A8 | 5/2008 |
| WO | WO 08149232 A2 | 12/2008 |
| WO | WO 08149232 A3 | 12/2008 |
| WO | WO 09155115 A2 | 12/2009 |
| WO | WO 09155115 A3 | 12/2009 |
| WO | WO 10022353 A1 | 2/2010 |

OTHER PUBLICATIONS

Article—Lawton et al, "High-Temperature Short-Time Extrusion of Wheat Gluten and a Bran-Like Fraction," *Cereal Chem.*, vol. 62, No. 4, 1985, pp. 267-271.

Article—Liu et al., "Modifications of Soy Protein Plastic with Functional Monomer with Reactive Extrusion," *J. Polym. Environ.*, vol. 16, No. 3, 2008, pp. 177-182.

Article—Mastromatteo et al., "Controlled release of thymol from zein based film," *Innovative Food Science and Emerging Technologies*, vol. 10, 2009, pp. 222-227.

Article—Nobile et al., "Active packaging by extrusion processing of recyclable and biodegradable polymers," *Journal of Food Engineering*, vol. 93, 2009, pp. 1-6.

Article—Nobile et al., "Antimicrobial efficacy and release kinetics of thymol from zein films," *Journal of Food Engineering*, vol. 89, 2008, pp. 57-63.

Article—O'Lenick, Jr., Anthony J., "Silicone Emulsions and Surfactants—A Review," *Silicone Spectator*, May 2000, 18 pages.

Article—Parris, et al., "Encapsulation of Essential Oils in Zein Nanospherical Particles," *J. Agric. Food Chem.*, vol. 53, No. 12, Jun. 15, 2005, pp. 4788-4792.

(56) References Cited

OTHER PUBLICATIONS

Article—Redl et al., "Extrusion of Wheat Gluten Plasticized with Glycerol: Influence of Process Conditions on Flow Behavior, Rheological Properties, and Molecular Size Distribution," *Cereal Chem.*, vol. 76, No. 3, 1999, pp. 361-370.
Article—Sanchez-Garcia et al., "Novel Polycaprolactone Nanocomposites Containing Thymol of Interest in Antimicrobial Film and Coating Applications," *Journal of Plastic Film and Sheeting*, vol. 24, Jul.-Oct. 2008, pp. 239-251.
Article—Ullsten et al, "Enlarged Processing Window of Plasticized Wheat Gluten Using Salicylic Acid," *Biomacromolecules*, vol. 7, No. 3, 2006, pp. 771-776.
Article—Vaz et al., "Soy Matrix Drug Delivery Systems Obtained by Melt-Processing Techniques," *Biomacromolecules*, vol. 4, No. 6, Nov./Dec. 2003, pp. 1520-1529.
Article—Verbeek et al., "Extrusion Processing and Properties of Protein-Based Thermoplastics," *Macromolecular Materials and Engineering*, vol. 295, 2010, pp. 10-21.
Paper entitled "Chemistry of Crosslinking" from Thermo Fisher Scientific, Inc., 2010, 8 pages.
Presentation to the Midwest Chapter of the Society of Cosmetic Chemists—The HLB System—A Time Saving Guide to Surfactant Selection, Mar. 9, 2004, by Uniqema, 39 pages.
ASTM D 445-04—Standard Test Method for Kinematic Viscosity of Transparent and Opaque Liquids (and the Calculation of Dynamic Viscosity), Current edition approved May 1, 2004, originally approved in 1937.
ASTM 5034 95—Standard Test Method for Breaking Strength and Elongation of Textile Fabrics (Grab Test), Current edition approved May 15, 1995.
Related U.S. Patent Applications Form.

\* cited by examiner

WIPE COATED WITH A BOTANICAL COMPOSITION HAVING ANTIMICROBIAL PROPERTIES

BACKGROUND OF THE INVENTION

Many existing wipes are impregnated with an antimicrobial solution for delivery to a contaminated surface. Unfortunately, however, many of the antimicrobial actives used in such wipes are undesirable due to their lack of environmental compatibility. While essential oils are known to be environmentally friendly and effective in combating microorganisms, they nevertheless suffer from significant problems. For example, essential oils are highly volatile and unstable in the presence of oxygen, which ultimately limits their effectiveness in most applications in which wipes are commonly employed (e.g., food service wipes). Attempts to overcome this problem often involve the use of a larger amount of the essential oils to prolong antimicrobial activity. Regrettably, this often just leads to another problem in that high concentrations of essential oils can cause damage to certain types of food products, such as fruit. As such, a need currently exists for an improved formulation for use in wipes that is safe, stable, and capable of providing antimicrobial activity over a period of time.

SUMMARY OF THE INVENTION

In accordance with one embodiment of the present invention, a wipe is disclosed that comprises a web that includes a plurality of fibers. The web is coated with an antimicrobial composition that comprises a botanical oil that is at least partially encapsulated by a film-forming protein. The composition forms a discontinuous coating on at least a portion of the fibers of the web.

In accordance with another embodiment of the present invention, a method for forming an antimicrobial wipe is disclosed. The method comprises forming a coating solution that comprises a botanical oil, protein, and a solvent, applying the coating solution to a web that includes a plurality of fibers, and drying the coating solution to form an antimicrobial coating on the web.

In accordance with yet another embodiment of the present invention, a method for inhibiting the growth of bacteria on a surface is disclosed. The method comprises contacting the surface with a wipe. The wipe comprises a web that includes a plurality of fibers. The web is coated with an antimicrobial composition that comprises a botanical oil that is at least partially encapsulated by a film-forming protein.

In accordance with yet another embodiment of the present invention, an antimicrobial concentrate is disclosed that has a solvent content of about 5 wt. % or less. The concentrate comprises at least one monoterpene phenol in an amount of from 0.05 wt. % to about 50 wt. %, at least one film-forming protein in an amount of from about 5 wt. % to about 50 wt. %, and at least one organopolysiloxane in an amount of from about 10 wt. % to about 70 wt. %. The protein at least partially encapsulates the monoterpene phenol.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
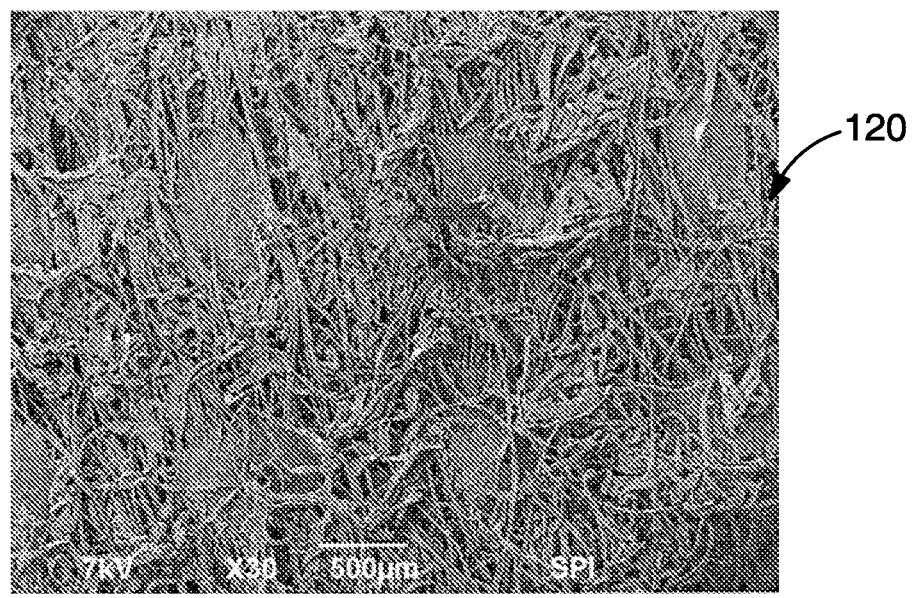
FIG. 1 is an SEM microphotograph of the coated substrate of Example 1, taken at a magnification of 30×.

Repeat use of references characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a wipe that contains a fibrous web on which is coated an antimicrobial composition. The composition includes a botanical oil derived from a plant (e.g., thymol, carvacrol, etc.). Because the botanical oil is volatile and tends to evaporate and lose efficacy during storage and prior to use, a protein is also employed in the composition to enhance long term stability of the oil and, in turn, its antimicrobial efficacy. Without intending to be limited by theory, it is believed that the protein can effectively encapsulate the botanical oil and inhibit its premature release. The use of a protein also enhances the biodegradability and renewability of the resulting wipe. The protein is also "film-forming" in the sense that it tends to form a substantially continuous film when coated onto a surface of the fibrous web. Because such proteins are typically stiff and brittle in nature, a continuous film would restrict the ability of the fibers to move and bend, thereby reducing web flexibility and drape. Thus, it is typically desired that the antimicrobial composition form a discontinuous coating on the fibrous web. In this regard, the present inventors have surprisingly discovered that the addition of an organopolysiloxane can help achieve such a discontinuous coating without adversely impacting the ability of the protein to stabilize the botanical oil. Without intending to be limited by theory, it is believed that the hydrophobic nature of the organopolysiloxane can result in hydrophobic interactions with the protein molecules to minimize to the ability of the protein to form a continuous film. The organopolysiloxane may also enhance the softness and overall handfeel of the wipe.

Various embodiments of the present invention will now be described in more detail below.

I. Antimicrobial Composition

A. Botanical Oil

Botanical oils are employed in the composition of the present invention as antimicrobial actives. The oil may be an "essential" oil that is extracted from a plant. Likewise, the botanical oil may also be isolated or purified from an essential oil, or it may simply be made synthetically to mimic a compound derived from a plant (e.g., synthetically made thymol). The botanical oils are generally soluble in lipids and believed to exhibit antimicrobial efficacy due to their ability to cause damage to the lipid component of the cell membrane in microorganisms, thereby inhibiting their proliferation. Essential oils are derived from herbs, flowers, trees, and other plants, and are typically present as tiny droplets between the cells of the plants and may be extracted by methods known to those of skill in the art (e.g., steam distillation, enfleurage (i.e., extraction using fat(s)), maceration, solvent extraction, or mechanical pressing). Examples of suitable essential oils for use in the present invention may include, for instance, anise oil, lemon oil, orange oil, oregano, rosemary oil, wintergreen oil, thyme oil, lavender oil, clove oil, hops, tea tree oil, citronella oil, wheat oil, barley oil, lemongrass oil, cedar leaf oil, cedar wood oil, cinnamon oil, fleagrass oil, geranium oil, sandalwood oil, violet oil, cranberry oil, eucalyptus oil, vervain oil, peppermint oil, gum benzoin, basil oil, fennel oil, fir oil, balsam oil, menthol, ocmea *origanum* oil, *Hydastis carradensis* oil, *Berberidaceae daceae* oil, *Ratanhiae* and *Curcuma longa* oil, sesame oil, *macadamia* nut oil, evening primrose oil, Spanish sage oil, Spanish rosemary oil, coriander oil, thyme oil, pimento berries oil, rose oil, bergamot oil, rosewood oil, chamomile oil, sage oil, clary sage oil, cypress oil, sea fennel oil, frankincense oil, ginger oil, grapefruit oil, jasmine oil, juniper oil, lime oil, mandarin oil, marjoram oil, myrrh oil, neroli oil, patchouli oil, pepper oil, black pepper oil, petitgrain oil, pine oil, rose otto oil, spearmint oil, spikenard oil, vetiver oil, or ylang ylang. Still other essential oils known to those of skill in the art are also contemplated as being useful within the context of the present invention (e.g., International Cosmetic Ingredient Dictionary, 10$^{th}$ and 12$^{th}$ editions, 2004 and 2008, respectively, which are incorporated by reference).

In one embodiment, carvacrol and thymol-containing oils are purified from the species *Origanum vulgare* of a hirtum variety. Ideally this is a hybrid strain that produces high quality oils, but is not limited to this genus, species or strain. The oil extract may also be obtained from a plant of the genus *Nepeta* including, but not limited to the species *Nepeta racemosa* (catmint), *Nepeta citriodora, Nepeta elliptica, Nepeta hindostoma, Nepeta lanceolata, Nepeta leucophylla, Nepeta longiobracteata, Nepeta mussinii, Nepeta nepetella, Nepeta sibthorpii, Nepeta subsessilis* and *Nepeta tuberose, Thymus glandulosus, Thymus hyemalis, Thymus vulgaris* and *Thymus zygis*.

As indicated above, isolates and/or derivatives of essential oils may also be employed in the present invention. For example, monoterpene phenols are particularly suitable for use in the present invention, which may be isolated and purified from plant oil extracts, or made synthetically by known methods. Thymol (isopropyl-cresol) is one particularly suitable monoterpene phenol, which is a crystalline substance that has a boiling point of about 238° C. at atmospheric pressure. Carvacrol (isopropyl-o-cresol), an isomer of thymol, is another suitable compound. Carvacrol is a liquid with a boiling point of about 233° C. at atmospheric pressure. Thymol and carvacrol, as well as isomers thereof, may be derived from plant oil extracts or synthesized. For example, carvacrol may be synthesized by the reaction of nitrous acid with 1-methyl-2-amino-4-propyl benzene. In addition to being employed in an isolated or pre-synthesized form, essential oils containing the monoterpene phenols as major constituents may be employed, with the final concentrations of the monoterpene phenols being within the ranges provided herein. The term "major constituent" generally refers to those essential oils having monoterpene phenols in an amount of more than 50 wt. %. It is well-known in the art that such essential oils may also contain lesser amounts of other constituents, such as non-aromatic terpene compounds. Essential oils with organic phenolic compounds as the major constituent include, for example, anise oil, bay oil terpineless, clove bud, clove leaf, clove oil, clove stem, *origanum* oil, Peru balsam, pimento oil, and thyme oil.

B. Protein

The antimicrobial composition also contains a film-forming protein, such as a vegetable protein, dairy protein, animal protein, as well as concentrates or isolates thereof. The protein source may be, for instance, milk (e.g., casein or caeseinates), whey, corn (e.g., zein), wheat (e.g., wheat gluten), soy, or other vegetable or animal sources. Plant proteins are particularly suitable for use in the present invention, such as zein, corn gluten, wheat gluten, whey protein, soy protein, etc. Any form of protein may be used, such as isolates, concentrates and flour. For example, soy proteins may be in the form of an isolate containing from about 75 wt. % to about 98 wt. % protein, a concentrate containing from about 50 wt. % to about 75 wt. % protein, or flour containing from about 30 wt. % to about 50 wt. % protein. In certain embodiments, it is desirable to use a protein that is relatively pure, such as those having a protein content of about 75 wt. % or more, and in some cases, about 85 wt. % or more. Gluten proteins, for instance, may be purified by washing away any associated starch to leave a composite of gliadin and glutenin proteins. In one particular embodiment, a vital wheat gluten is employed. Such vital wheat gluten is commercially available as a creamy-tan powder produced from wheat flour by drying freshly washed gluten. For instance, vital wheat gluten can be obtained from Archer Daniels Midland ("ADM") of Decatur, Ill. under the designations WhetPro® 75 or 80. Similarly, purified soy protein isolates may be prepared by alkaline extraction of a defatted meal and acid precipitation, a technique well-known and used routinely in the art. Such purified soy proteins are commercially available from ADM under the designation PRO-FAM®, which typically have a protein content of 90 wt. % or more. Other purified soy protein products are also available from DuPont of Louisville, Ky. under the designation PRO-COTE® and from Central Soya under the designation Promie R.

If desired, the protein may also be modified using techniques known in the art to improver its ability to disperse in aqueous solutions. Suitable modification techniques may include pH modification, denaturation, hydrolysis, acylation, reduction, oxidation, etc. Just as an example, gluten may sometimes absorb water until it begins to repel excess water. This results in gluten molecules that are associated closely together resist dispersion in aqueous solutions. To counteract this tendency, the protein may be treated with a pH modifier to increase its solubility in aqueous environments. Typically, the pH modifier is a basic reagent that can raise the pH of the protein, thereby causing it to become more soluble in aqueous solutions. Monovalent cation-containing basic reagents (hereafter "monovalent basic reagents") are particularly suitable for use in the present invention. Examples of such monovalent basic reagents include, for instance, alkali metal hydroxides (e.g., sodium hydroxide, ammonium hydroxide, etc.), ammonia, etc. Of course, multivalent reagents, such as alkaline metal hydroxides (e.g., calcium hydroxide) and alkaline metal oxides (e.g., calcium oxide), may also be employed if desired.

Hydrolysis of the protein material may also improve water solubility, and can be effected by treating the protein with a hydrolytic enzyme. Many enzymes are known in the art which hydrolyze protein materials, including, but not limited to, proteases, pectinases, lactases, and chymotrypsin. Enzyme hydrolysis is effected by adding a sufficient amount of enzyme to an aqueous dispersion of protein material, typically from about 0.1% to about 10% enzyme by weight of the protein material, and treating the enzyme and protein dispersion. After sufficient hydrolysis has occurred the enzyme may be deactivated by heating, and the protein material may be precipitated from the solution by adjusting the pH of the solution to about the isoelectric point of the protein material.

C. Carbohydrate Polymers

Carbohydrate polymers may optionally be employed in the present invention in combination with the protein. Among other things, the use of such carbohydrate polymers may further enhance the stability of the botanical oil during use. Carbohydrate polymers include both natural and/or synthetic carbohydrate polymers. Suitable carbohydrate polymers with hydroxyl functional groups may include, for instance, starch, amylose, dextran, chitin, pullulan, gellan gum, xylan, galactomannan, carrageenan, agar, locust bean gum, guar gum, gum arabic, pectin, methylcellulose, ethylcellulose, hydroxyethylcellulose, hydroxypropylcellulose, ethylhydroxyethylcellulose, hydroxybutylmethylcellulose, hydroxyethylmethylcellulose, etc., as well as derivatives and/or mixtures thereof. Suitable examples of biopolymers with carboxyl functional groups may include, for instance, alginate, xanthan, hyaluronic acid, heparin, chondroitin sulfate, keratan, dermatan, oxidized cellulose, carboxymethylcellulose, carboxymethyl starch, etc., as well as derivatives and/or mixtures thereof. Suitable examples of biopolymers with amino functional groups may include, for instance, chitosan and other polysaccharides which include in their structure glycosamines residues, in natural or diacetylated form, collagen, collagenic biopolymers (e.g., atelocollagen, solubilized collagen, gelatin and collagen hydrolysate), keratin hydrolysate, fibrin, fibroin, ovalbumine, bovine serumalbumine, zein, gluten, casein, soy protein, heparosan, hyalurosan, etc., as well as derivatives and/or mixtures thereof.

Starch polymers are particularly suitable for use as carbohydrate polymers as they are derived from plants, biodegradable, renewable, and also capable of being readily modified to enhance their water-sensitivity. Although starch polymers are produced in many plants, typical sources includes seeds of cereal grains, such as corn, waxy corn, wheat, sorghum, rice, and waxy rice; tubers, such as potatoes; roots, such as tapioca (i.e., cassava and manioc), sweet potato, and arrowroot; and the pith of the sago palm. Chemically modified starches are particularly desirable in the present invention. Without intending to be limited by theory, it is believed that such modified starches possess polar groups (e.g., hydroxy) and nonpolar groups (e.g., alkyl) that are capable of interacting with the polar (e.g., phenolic hydroxyl) and nonpolar (e.g. isopropyl) groups, respectively, found in monoterpene phenolic botanical oils. This enhances the ability of the starch polymer to trap and hold the botanical oil prior to use. Furthermore, the modification of the starch polymer provides enhanced chain flexibility, which even further enhances its trapping efficiency. Such chemically modified starches may be obtained through typical processes known in the art (e.g., esterification, etherification, oxidation, acid hydrolysis, enzymatic hydrolysis, etc.). Starch ethers and/or esters may be particularly desirable, such as hydroxyalkyl starches, carboxymethyl starches, etc. The hydroxyalkyl group of hydroxyalkyl starches may contain, for instance, 2 to 10 carbon atoms, in some embodiments from 2 to 6 carbon atoms, and in some embodiments, from 2 to 4 carbon atoms. Representative hydroxyalkyl starches such as hydroxyethyl starch, hydroxypropyl starch, hydroxybutyl starch, and derivatives thereof. Starch esters, for instance, may be prepared using a wide variety of anhydrides (e.g., acetic, propionic, butyric, and so forth), organic acids, acid chlorides, or other esterification reagents. The degree of esterification may vary as desired, such as from 1 to 3 ester groups per glucosidic unit of the starch.

The starch polymer may contain different weight percentages of amylose and amylopectin, different polymer molecular weights, etc. High amylose starches contain greater than about 50% by weight amylose and low amylose starches contain less than about 50% by weight amylose. Although not required, low amylose starches having an amylose content of from about 10% to about 40% by weight, and in some embodiments, from about 15% to about 35% by weight, are particularly suitable for use in the present invention. Examples of such low amylose starches include corn starch and potato starch, both of which have an amylose content of approximately 20% by weight. Particularly suitable low amylose starches are those having a number average molecular weight ("$M_n$") ranging from about 50,000 to about 1,000,000 grams per mole, in some embodiments from about 75,000 to about 800,000 grams per mole, and in some embodiments, from about 100,000 to about 600,000 grams per mole, and/or a weight average molecular weight ("$M_w$") ranging from about 5,000,000 to about 25,000,000 grams per mole, in some embodiments from about 5,500,000 to about 15,000,000 grams per mole, and in some embodiments, from about 6,000,000 to about 12,000,000 grams per mole. The ratio of the weight average molecular weight to the number average molecular weight ("$M_w/M_n$"), i.e., the "polydispersity index", is also relatively high. For example, the polydispersity index may range from about 10 to about 100, and in some embodiments, from about 20 to about 80. The weight and number average molecular weights may be determined by methods known to those skilled in the art.

D. Organopolysiloxane

The organopolysiloxanes of the present invention may have a linear, partially branched, or a branched structure. Silicon-bonded organic groups used in these polymers may contain monovalent hydrocarbon and/or monovalent halogenated hydrocarbon groups. Such monovalent groups typically have from 1 to about 20 carbon atoms, preferably from 1 to 10 carbon atoms, and are exemplified by, but not limited to, alkyl (e.g., methyl, ethyl, propyl, pentyl, octyl, undecyl, and octadecyl); cycloalkyl (e.g., cyclohexyl); alkenyl (e.g., vinyl, allyl, butenyl, and hexenyl); aryl (e.g., phenyl, tolyl, xylyl, benzyl, and 2-phenylethyl); and halogenated hydrocarbon groups (e.g., 3,3,3-trifluoropropyl, 3-chloropropyl, and dichlorophenyl). Preferably, at least 50%, and more preferably at least 80%, of the organic groups are methyl. Examples of such methylpolysiloxanes may include, for instance, polydimethylsiloxane ("PDMS"), polymethylhydrogensiloxane, etc. Still other suitable methyl polysiloxanes may include dimethyldiphenylpolysiloxane, dimethyl/methylphenylpolysiloxane, polymethylphenylsiloxane, methylphenyl/dimethylsiloxane, vinyldimethyl terminated polydimethylsiloxane, vinylmethyl/dimethylpolysiloxane, vinyldimethyl terminated vinylmethyl/dimethylpolysiloxane, divinylmethyl terminated polydimethylsiloxane, vinylphenylmethyl terminated polydimethylsiloxane, dimethylhydro terminated polydimethylsiloxane, methylhydro/dimethylpolysiloxane, methylhydro terminated methyloctylpolysiloxane, methylhydro/phenylmethyl polysiloxane, etc.

As indicated above, the present inventors believe the hydrophobic portion of the organopolysiloxane can interact with the protein molecules to facilitate the formation of a discontinuous coating on the fibrous web. Nevertheless, in certain embodiments, the organopolysiloxane may also contain one more pendant and/or terminal polar functional groups, such as hydroxyl, epoxy, carboxyl, amino, alkoxy, methacrylic, or mercapto groups, which impart some degree of hydrophilicity to the polymer. Without intending to be limited by theory, the present inventors believe that such polar functional groups can aid in the ability to disperse the polymer in aqueous solutions. For example, the organopolysiloxane may contain at least one hydroxy group, and preferably an average of at least two silicon-bonded hydroxy groups (silanol groups) per molecule. One particularly suitable hydroxy-modified organopolysiloxane, for example, is a hydroxy-terminated polydiorganosiloxane having the general formula $HOR^1_2SiO(R^1_2SiO)_mSiR^1_2OH$, wherein each $R^1$ is independently selected from monovalent hydrocarbon and monovalent halogenated hydrocarbon groups, such as described above, and wherein m is greater than 0, such as from 1 to 10,000. Preferably, each $R^1$ is methyl. Examples of such organopolysiloxanes include, for instance, dihydroxypolydimethylsiloxane, hydroxy-trimethylsiloxypolydimethylsiloxane, etc. Other examples of hydroxyl-modified organopolysiloxanes are described in U.S. Patent Application Publication No. 2003/0105207 to Kleyer, et al., which is incorporated herein in its entirety by reference thereto for all purposes. Alkoxy-modified organopolysiloxanes may also be employed, such as dimethoxypolydimethylsiloxane, methoxy-trimethylsiloxypolydimethylsiloxane, diethoxypolydimethylsiloxane, ethoxy-trimethylsiloxy-polydimethylsiloxane, etc. Still other suitable organopolysiloxanes are those modified with at least one amino functional group. Examples of such amino-functional polysiloxanes include, for instance, diamino-functional polydimethylsiloxanes. Various other suitable polar functional groups for organopolysiloxanes are also described in U.S. Patent Application Publication No. 2010/00234517 to Plantenberg, et al., which is incorporated herein in its entirety by reference thereto for all purposes.

Although not necessarily required, the organopolysiloxane may be employed in the form of an emulsion that is optionally pre-formed prior to incorporation of the polymer into the coating solution. Such emulsions may include one or more aqueous solvents, such as water. The silicone emulsion may also contain non-aqueous solvents which, although not required, can aid in dissolving certain components of the emulsion. Examples of some suitable non-aqueous solvents include, but are not limited to, glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations thereof. The amount of solvent utilized in the emulsion may generally vary depending on the relative amounts of the other components present within the formulation. When utilized, the solvent is typically present in the formulation in an amount from about 20 wt. % to about 99.99 wt. %, and in some embodiments, from about 50 wt. % to about 98 wt. % of the emulsion.

An optional emulsifier system may also be employed to help create a uniform dispersion of the organopolysiloxane. The emulsifier system may include one or more nonionic, anionic, and/or amphoteric emulsifiers, including mixtures containing different species or mixtures of different surfactants within the same species. Nonionic surfactants, which typically have a hydrophobic base (e.g., long chain alkyl group or an alkylated aryl group) and a hydrophilic chain (e.g., chain containing ethoxy and/or propoxy moieties), are particularly suitable. Some suitable nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglyceride or diglycerides of long chain alcohols, and mixtures thereof. Particularly suitable nonionic emulsifiers may include ethylene oxide condensates of fatty alcohols (e.g., sold under the trade name Lubrol), polyoxyethylene ethers of fatty acids (particularly $C_{12}$-$C_{20}$ fatty acids), polyoxyethylene sorbitan fatty acid esters (e.g., sold under the trade name TWEEN®), and sorbitan fatty acid esters (e.g., sold under the trade name SPAN™ or ARLACEL®), etc. The fatty components used to form such emulsifiers may be saturated or unsaturated, substituted or unsubstituted, and may contain from 6 to 22 carbon atoms, in some embodiments from 8 to 18 carbon atoms, and in some embodiments, from 12 to 14 carbon atoms.

The solids content of the emulsion may generally be varied to achieve the desired properties. For example, the emulsion may have a solids content of from about 1 wt. % to about 70 wt. %, in some embodiments from about 5 wt. % to about 60 wt. %, and in some embodiments, from about 10 wt. % to about 55 wt. %. To lower the solids content of a commercially available silicone emulsion, additional amounts of solvent may be utilized. The emulsion may also have a relatively low viscosity to provide for minor entanglement of the polysiloxane chain. For example, the emulsion may have a kinematic viscosity of about 50,000 centistokes or less, in some embodiments from about 250 to about 30,000 centistokes, and in some embodiments, from about 500 to about 10,000 centistokes. The kinematic viscosity is the absolute viscosity of the additive divided by its density at the same temperature of measurement, and is determined according to ASTM D445 at 25° C. Apparent viscosities may likewise vary in the range of from about 50 to about 500 centipoise, in some embodiments from about 75 to about 450 centipoise, and in some embodiments, from about 100 to about 400 centipoise, determined at a temperature of 25° C. Particular examples of organpolysiloxane emulsions that may be employed in the present invention are available from Dow Corning Korea, Ltd. under the designations TM-4865 (PDMS), TM-4866 (hydroxy-terminated PDMS), TM-4829 (amino-functional siloxane), and TM-7920 (dimethyl vinyl-terminated PDMS).

E. Other Components

In addition to those noted above, still other additives may also be incorporated into the composition. For example, the composition may contain a preservative or preservative system to inhibit the growth of microorganisms over an extended period of time. Suitable preservatives may include, for instance, alkanols, disodium EDTA (ethylenediamine tetraacetate), EDTA salts, EDTA fatty acid conjugates, isothiazolinone, benzoic esters (parabens) (e.g., methylparaben, propylparaben, butylparaben, ethylparaben, isopropylparaben, isobutylparaben, benzylparaben, sodium methylparaben, and sodium propylparaben), benzoic acid, propylene glycols, sorbates, urea derivatives (e.g., diazolindinyl urea), and so forth. Other suitable preservatives include those sold by Sutton Labs, such as "Germall 115" (amidazolidinyl urea), "Germall II" (diazolidinyl urea), and "German Plus" (diazolidinyl urea and iodopropynyl butylcarbonate). Another suitable preservative is Kathon CG®, which is a mixture of methylchloroisothiazolinone and methylisothiazolinone available from Rohm & Haas; Mackstat H 66 (available from McIntyre Group, Chicago, Ill.). Still another suitable preservative system is a combination of 56% propylene glycol, 30% diazolidinyl urea, 11% methylparaben, and 3% propylparaben available under the name GERMABEN® II from International Specialty Products of Wayne, N.J.

The pH of the composition may also be controlled within a range that is considered more biocompatible. For instance, it is typically desired that the pH is within a range of from about 3 to about 9, in some embodiments from about 4 to about 8, and in some embodiments, from about 5 to about 7. Various pH modifiers may be utilized in the composition to achieve the desired pH level. Some examples of pH modifiers that may be used in the present invention include, but are not limited to, mineral acids, sulfonic acids (e.g., 2-[N-morpholino]ethane sulfonic acid), carboxylic acids, and polymeric acids. Specific examples of suitable mineral acids are hydrochloric acid, nitric acid, phosphoric acid, and sulfuric acid. Specific examples of suitable carboxylic acids are lactic acid, acetic acid, citric acid, glycolic acid, maleic acid, gallic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly(methacrylic) acid, and naturally occurring polymeric acids such as carageenic acid, carboxymethyl cellulose, and alginic acid. Basic pH modifiers may also be used in some embodiments of the present invention to provide a higher pH value. Suitable pH modifiers may include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; monoethanolamine; triethylamine; isopropanolamine; diethanolamine; and triethanolamine. When utilized, the pH modifier may be present in any effective amount needed to achieve the desired pH level.

To better enhance the benefits to consumers, other optional ingredients may also be used. For instance, some classes of ingredients that may be used include, but are not limited to: antioxidants (product integrity); anti-reddening agents, such as aloe extract; astringents—cosmetic (induce a tightening or tingling sensation on skin); colorants (impart color to the product); deodorants (reduce or eliminate unpleasant odor and protect against the formation of malodor on body surfaces); fragrances (consumer appeal); opacifiers (reduce the clarity or transparent appearance of the product); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); and thickeners (to increase viscosity).

II. Coating Solution

The ingredients of the antimicrobial composition are generally incorporated into a coating solution prior to being applied to the wipe. The manner in which the solution is formed may vary as is known to those skilled in the art. In one embodiment, for example, the proteins may be initially blended with a solvent, such as water or an organic solvent. Organic solvents are particularly desired for use in the present invention, such as alcohols, such as methanol, ethanol, n-propanol, isopropanol, butanol, and so forth; triglycerides; ketones (e.g., acetone, methyl ethyl ketone, and methyl isobutyl ketone); esters (e.g., ethyl acetate, butyl acetate, diethylene glycol ether acetate, and methoxypropyl acetate); amides (e.g., dimethylformamide, dimethylacetamide, dimethylcaprylic/capric fatty acid amide and N-alkylpyrrolidones); nitriles (e.g., acetonitrile, propionitrile, butyronitrile and benzonitrile); sulfoxides or sulfones (e.g., dimethyl sulfoxide (DMSO) and sulfolane); and so forth. Thereafter, the oil components (e.g., botanical oil and organopolysiloxane emulsion) may then be combined with the solvent mixture. The combination of the ingredients may be facilitated through agitation (e.g., stirring) and control of the temperatures of each mixture. Conventional homogenization techniques may, for instance, be employed to stabilize the solution.

The resulting coating solution may contain a discontinuous oil phase dispersed within a continuous solvent phase. Nevertheless, due to the stability imparted by the protein, a relatively small amount of botanical oils may be employed and still achieve the desired antimicrobial efficacy. More particularly, the coating solution may employ botanical oils in an amount of from about 0.05 wt. % to about 15 wt. %, in some embodiments from about 0.5 wt. % to about 10 wt. %, and in some embodiments, from about 1 wt. % to about 5 wt. %. The coating solution may also contain proteins in an amount of from about 0.1 wt. % to about 15 wt. %, in some embodiments from about 0.5 wt. % to about 10 wt. %, and in some embodiments, from about 1 wt. % to about 5 wt. %. If desired, carbohydrate polymers may also be employed in the coating solution, such as in an amount of from about 0.1 wt. % to about 15 wt. %, in some embodiments from about 0.5 wt. % to about 10 wt. %, and in some embodiments, from about 1 wt. % to about 5 wt. %.

Organopolysiloxanes may also constitute from about 0.1 wt. % to about 25 wt. %, in some embodiments from about 0.5 wt. % to about 20 wt. %, and in some embodiments, from about 1 wt. % to about 15 wt. % of the coating solution. When employed in the form of an emulsion, the organopolysiloxane emulsion may itself constitute from about 0.5 wt. % to about 30 wt. %, in some embodiments from about 1 wt. % to about 25 wt. %, and in some embodiments, from about 2 wt. % to about 20 wt. % of the solution. Solvents may likewise constitute from about 60 wt. % to about 99 wt. %, in some embodiments from about 70 wt. % to about 95 wt. %, and in some embodiments, from about 75 wt. % to about 95 wt. %.

III. Wipe

Although the coating may be administered in a variety of forms, such as a lotion, cream, jelly, liniment, ointment, salve, oil, foam, gel, film, wash, coating, liquid, capsule, tablet, concentrate, etc., it is typically desired that is applied to a wipe prior to use. Such wipes may be used to reduce microbial or viral populations on a hard surface (e.g., sink, table, counter, sign, and so forth) or surface on a user/patient (e.g., skin, mucosal membrane, such as in the mouth, nasal passage, stomach, vagina, etc., wound site, surgical site, and so forth). The wipe may provide an increased surface area to facilitate contact of the composition with microorganisms. In addition, the wipe may also serve other purposes, such as providing water absorption, barrier properties, etc. The wipe may also eliminate microorganisms through shear forces imparted to the surface.

The wipe may be formed from any of a variety of materials as is well known in the art. Typically, however, the wipe includes a fibrous web that contains absorbent fibers. For example, the wipe may be a paper product containing one or more paper webs, such as facial tissue, bath tissue, paper towels, napkins, and so forth. The paper product may be single-ply in which the web forming the product includes a single layer or is stratified (i.e., has multiple layers), or multi-ply, in which the webs forming the product may themselves be either single or multi-layered. Normally, the basis weight of such a paper product is less than about 120 grams per square meter ("gsm"), in some embodiments less than about 80 gsm, in some embodiments less than about 60 grams per square meter, and in some embodiments, from about 10 to about 60 gsm.

Any of a variety of materials can also be used to form the paper web(s) of the product. For example, the material used to make the paper product may include absorbent fibers formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Exemplary commercially available pulp fibers suitable for the present invention include those available from Kimberly-Clark Corporation under the trade designations "Longlac-19", Hardwood fibers, such as eucalyptus, maple, birch, aspen, and so forth, can also be used. In certain instances, eucalyptus fibers may be particularly desired to increase the softness of the web. Eucalyptus fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other natural fibers can also be used in the present invention, such as abaca, sabai grass, milkweed floss, pineapple leaf, bamboo, algae, and so forth. In addition, in some instances, synthetic fibers can also be utilized.

If desired, the absorbent fibers (e.g., pulp fibers) may be integrated with synthetic fibers to form a composite. Synthetic thermoplastic fibers may also be employed in the nonwoven web, such as those formed from polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; polyhydroxyalkanoate; copolymers thereof; and so forth. Because many synthetic thermoplastic fibers are inherently hydrophobic (i.e., non-wettable), such fibers may optionally be rendered more hydrophilic (i.e., wettable) by treatment with a surfactant solution before, during, and/or after web formation. Other known methods for increasing wettability may also be employed, such as described in U.S. Pat. No. 5,057,361 to Sayovitz, et al., which is incorporated herein in its entirety by reference thereto for all purposes. The relative percentages of such fibers may vary over a wide range depending on the desired characteristics of the composite. For example, the composite may contain from about 1 wt. % to about 60 wt. %, in some embodiments from 5 wt. % to about 50 wt. %, and in some embodiments, from about 10 wt. % to about 40 wt. % synthetic polymeric fibers. The composite may likewise contain from about 40 wt. % to about 99 wt. %, in some embodiments from 50 wt. % to about 95 wt. %, and in some embodiments, from about 60 wt. % to about 90 wt. % absorbent fibers.

Composites, such as described above, may be formed using a variety of known techniques. For example, a nonwoven composite may be formed that is a "coform material" that contains a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes. Alternatively, the nonwoven composite may be formed be formed by hydraulically entangling staple length fibers and/or filaments with high-pressure jet streams of water. Various techniques for hydraulically entangling fibers are generally are disclosed, for example, in U.S. Pat. No. 3,494,821 to Evans and U.S. Pat. No. 4,144,370 to Bouolton, which are incorporated herein in their entirety by reference thereto for all purposes. Hydraulically entangled nonwoven composites of continuous filaments (e.g., spunbond web) and natural fibers (e.g., pulp) are disclosed, for example, in U.S. Pat. No. 5,284,703 to Everhart, et al. and U.S. Pat. No. 6,315,864 to Anderson, et al., which are incorporated herein in their entirety by reference thereto for all purposes. Hydraulically entangled nonwoven composites of staple fiber blends (e.g., polyester and rayon) and natural fibers (e.g., pulp), also known as "spunlaced" fabrics, are described, for example, in U.S. Pat. No. 5,240,764 to Haid, et al., which is incorporated herein in its entirety by reference thereto for all purposes.

Regardless of the materials or processes utilized to form the wipe, the basis weight of the wipe is typically from about 20 to about 200 grams per square meter ("gsm"), and in some embodiments, between about 35 to about 100 gsm. Lower basis weight products may be particularly well suited for use as light duty wipes, while higher basis weight products may be better adapted for use as industrial wipes.

The wipe may assume a variety of shapes, including but not limited to, generally circular, oval, square, rectangular, or irregularly shaped. Each individual wipe may be arranged in a folded configuration and stacked one on top of the other to provide a stack of wet wipes. Such folded configurations are well known to those skilled in the art and include c-folded, z-folded, quarter-folded configurations and so forth. For example, the wipe may have an unfolded length of from about 2.0 to about 80.0 centimeters, and in some embodiments, from about 10.0 to about 25.0 centimeters. The wipes may likewise have an unfolded width of from about 2.0 to about 80.0 centimeters, and in some embodiments, from about 10.0 to about 25.0 centimeters. The stack of folded wipes may be placed in the interior of a container, such as a plastic tub, to provide a package of wipes for eventual sale to the consumer. Alternatively, the wipes may include a continuous strip of material which has perforations between each wipe and which may be arranged in a stack or wound into a roll for dispensing. Various suitable dispensers, containers, and systems for delivering wipes are described in U.S. Pat. No. 5,785,179 to Buczwinski, et al.; U.S. Pat. No. 5,964,351 to Zander; U.S. Pat. No. 6,030,331 to Zander; U.S. Pat. No. 6,158,614 to Haynes, et al.; U.S. Pat. No. 6,269,969 to Huang, et al.; U.S. Pat. No. 6,269,970 to Huang, et al.; and U.S. Pat. No. 6,273,359 to Newman, et al., which are incorporated herein in their entirety by reference thereto for all purposes.

The coating solution of the present invention may be impregnated into the wipe during its formation or simply coated onto all or a portion of a surface of the wipe using known techniques, such as printing, dipping, spraying, melt extruding, coating (e.g., solvent coating, powder coating, brush coating, etc.), foaming, and so forth. In one embodiment, for example, the coating is applied to the wipe by dipping, spraying, or printing. As indicated above, one benefit of the present invention is that the composition may be applied in a film-like pattern that is discontinuous over the surface of the wipe. The pattern may, for example, cover only from about 5% to about 95%, in some embodiments from about 10% to about 90%, and in some embodiments, from about 20% to about 75% of a surface of the wipe. Such patterned application may have various benefits, including enhanced softness and drape, improved absorbency, etc.

If desired, the wipe may be dried at a certain temperature to drive the solvents from the solution and form a concentrate. Such concentrates generally have a very high stability in storage. To use the wipe, water or an aqueous solution may simply be added, thereby releasing the botanical oil and optionally re-emulsifying the concentrate. Drying may be accomplished using any known technique, such as an oven, drying rolls (e.g., through-air drying, Yankee dryer), etc. The temperature at which the wipe is dried generally depending on the time period over which it is dried, but is typically at least about 20° C., and in some embodiments, from about 30° C. to about 100° C. Drying may occur either before or after the solution is applied to the wipe. The solvent content of the resulting concentrate is thus typically less than about 5 wt. %, in some embodiments less than about 2 wt. %, and in some embodiments, less about 1 wt. %.

The solids add-on level of the solution is typically from about 2 to about 100%, in some embodiments from about 10% to about 80%, and in some embodiments, from about 15% to about 70%. The "solids add-on level" is determined by subtracting the weight of the untreated substrate from the weight of the treated substrate (after drying), dividing this calculated weight by the weight of the untreated substrate, and then multiplying by 100%. Lower add-on levels may provide optimum functionality of the substrate, while higher add-on levels may provide optimum antimicrobial efficacy. In such embodiments, the concentrate typically contains botanical oils in an amount of from about 0.05 wt. % to about 50 wt. %, in some embodiments from about 1 wt. % to about 40 wt. %, and in some embodiments, from about 5 wt. % to about 30 wt. %. The composition may also contain proteins in an amount of from about 5 wt. % to about 50 wt. %, in some embodiments from about 10 wt. % to about 40 wt. %, and in some embodiments, from about 20 wt. % to about 30 wt. %. Carbohydrate polymers may also be employed, such as in an amount of from about 5 wt. % to about 50 wt. %, in some embodiments from about 10 wt. % to about 40 wt. %, and in some embodiments, from about 20 wt. % to about 30 wt. %. Organopolysiloxanes may also constitute from about 10 wt. % to about 70 wt. %, in some embodiments from about 20 wt. % to about 60 wt. %, and in some embodiments, from about 30 wt. % to about 50 wt. % of the composition.

In addition to being employed as a concentrate, the coating may also be in the form of a liquid. This may be accomplished by simply not drying the solution after it is applied to the wipe. While the solids add-on level of such "wet wipes" generally remain within the ranges noted above, the total amount of the solution employed in such "wet wipes" (including any solvents) depends in part upon the type of wipe material utilized, the type of container used to store the wipes, the nature of the solution, and the desired end use of the wipes. Generally, however, each wet wipe contains from about 150 wt. % to about 600 wt. %, and desirably from about 300 wt. % to about 500 wt. % of the solution on the dry weight of the wipe.

The present inventors have discovered that the composition of the present invention may inhibit (e.g., reduce by a measurable amount or to prevent entirely) the growth of one or more microorganisms when exposed thereof. Examples of microorganisms that may be inhibited include bacteria (including cyanobacteria and *Mycobacteria*), protozoa, algae, fungi (e.g., molds and yeast), viruses, prions, and other infectious particles. For example, the coating may inhibit the growth of several medically significant bacterial groups, such as Gram negative rods (e.g., *Entereobacteria*); Gram negative curved rods (e.g., *Heliobacter, Campylobacter*, etc.); Gram negative cocci (e.g., *Neisseria*); Gram positive rods (e.g., *Bacillus, Clostridium*, etc.); Gram positive cocci (e.g., *Staphylococcus, Streptococcus*, etc.); obligate intracellular parasites (e.g., *Riccketttsia* and *Chlamydia*); acid fast rods (e.g., *Myobacterium, Nocardia*, etc.); spirochetes (e.g., *Treponema, Borellia*, etc.); and mycoplasmas (i.e., bacteria that lack a cell wall). Particularly species of bacteria that may be inhibited with the composition of the present invention include *Escherichia coli* (Gram negative rod), *Klebsiella pneumonia* (Gram negative rod), *Streptococcus* (Gram positive cocci), *Salmonella choleraesuis* (Gram negative rod), *Staphyloccus aureus* (Gram positive cocci), and *P. aeruginosa* (Gram negative rod). In addition to bacteria, other microorganisms of interest include fungi (e.g., *Aspergillus niger*) and yeasts (e.g., *Candida albicans*).

Upon exposure for a certain period of time, the composition may provide a log reduction of at least about 2, in some embodiments at least about 3, in some embodiments at least about 4, and in some embodiments, at least about 5 (e.g., about 6). Log reduction, for example, may be determined from the % population killed by the composition according to the following correlations:

| % Reduction | Log Reduction |
|---|---|
| 90 | 1 |
| 99 | 2 |
| 99.9 | 3 |
| 99.99 | 4 |

| % Reduction | Log Reduction |
|---|---|
| 99.999 | 5 |
| 99.9999 | 6 |

Such a log reduction may be achieved in accordance with the present invention after only a relatively short exposure time. For example, the desired log reduction may be achieved after exposure for only 30 minutes, in some embodiments 15 minutes, in some embodiments 10 minutes, in some embodiments 5 minutes, in some embodiments 1 minute, and in some embodiments, 30 seconds.

The present invention may be better understood with reference to the following examples.

Materials Employed

Thymol (98% of purity) and carvacrol (98% purity) were obtained from Sigma-Aldrich (Korea).
Glycerol was obtained from Sigma-Aldrich (Korea).
Soy Protein Isolates (90% protein, 6% moisture) were obtained from ADM (US) under the designation PRO-FAM® 974.
Zein was obtained from Sigma-Aldrich (Korea).
A polydimethylsiloxane ("PDMS") emulsion was obtained from Dow Corning (Korea) under the designation TM4855. The emulsion had a solids content of about 55 wt. %.
A hydroxy-terminated PDMS emulsion was obtained from Dow Corning (Korea) under the designation TM4856. The emulsion had a solids content of about 55 wt. %.
A HYDROKNIT® substrate (Kimberly-Clark) was employed that had a basis weight of 64 grams per square meter and contained 82 wt. % pulp fibers and 18 wt. % polypropylene spunbond fibers.

Test Methods

Carvacrol Stability

The residual carvacrol level on the substrate was determined through "High Performance Liquid Chromatography (HPLC) analysis." More particularly, the carvacrol level in each sample was determined by generating a carvacrol calibration curve using 99.5% pure carvactrol. The carvacrol levels were reported as an average of duplicate determinations and as a wt/wt basis, based on the weight of the substrate sample. Approximately 9 cm$^2$ of material was cut and weighed into a 20-mL vial for each code. To each vial, 10 milliliters of an isopropyl alcohol/water mixture (75:25) was added and the contents were shaken for ten (10) minutes to extract all of the carvacrol from the substrate. The resulting solutions were filtered through PTFE filters and used for analysis. The conditions used during HPLC are set forth below:
  Column: Phenomenex NH$_2$
  Column Temperature: Ambient
  Mobile Phase: 75:25 (Isopropyl alcohol:water)
  Flow rate: 0.6 milliliters per minute
  Injection volume: 100 microliters
  Run Time: 7 minutes
  UV detection: 280 nanometers
Thymol Stability
The residual thymol level on the substrate was determined through "High Performance Liquid Chromatography (HPLC) analysis." More particularly, the thymol level in each sample was determined by generating a thymol calibration curve using 99.5% pure thymol. The thymol levels were reported as an average of duplicate determinations and as a wt/wt basis, based on the weight of the substrate sample. Approximately 9 cm$^2$ of material was cut and weighed into a 20-mL vial for each code. To each vial, 10 milliliters of an ethanol/water mixture (90:10) was added and the contents were shaken for ten (10) minutes to extract all of the thymol from substrate. The resulting solutions were filtered through PTFE filters and used for analysis. The conditions used during HPLC are set forth below:
  Column: XTerra® MS C18 5 µm 3.0×100 mm
  Column Temperature: Ambient
  Mobile Phase: 80:20 (Ethanol:water)
  Flow rate: 0.3 milliliters per minute
  Injection volume: 10 microliters
  Run Time: 6 minutes
  UV detection: 277 nanometers
Zone of Inhibition
To determine antimicrobial efficacy, a zone of inhibition test was performed. More specifically, a sample of the coated substrate (about 1 cm$^2$ in area) was placed on a freshly spreading lawn of test microorganism on TSA (Trypticase Soy Agar). Two microorganisms were used, *Staphylococcus aureus* (ATCC #27660) as a Gram positive bacteria and *Escherichia coli* as a Gram negative bacteria (ATCC #25922). After 24 hours incubation at 37° C., plates were measured for clear zones of inhibition surrounding the each sample (Clear zone(mm)=diameter of clear zone−sample (wipe) diameter).
Cup Crush
The softness of a sample was measured according to the "cup crush" test. The cup crush test evaluates fabric softness by measuring the peak load required for a 4.5 cm diameter hemispherically shaped foot to crush a 23 cm by 23 cm piece of fabric shaped into an approximately 6.5 diameter by 6.5 cm tall inverted cup while the cup shaped fabric is surrounded by an approximately 6.5 cm diameter cylinder to maintain a uniform deformation of the cup shaped fabric. The foot and the cup are aligned to avoid contact between the cup walls and the foot which could affect the peak load. The peak load is measured while the foot is descending at a rate of about 38 cm per minute. The peak load value is measured in grams. A Model 3108-128 10 pound load cell (4.54 kg load cell) available from the MTS Systems Corporation of Cary, North is utilized in this test. The computer program, TestWorks 4 collected data during the test. A total of 5 to 8 repetitions were performed for each material and then averaged to give the reported values. Lower peak load values indicate a softer material.

Example 1

A coating solution was initially prepared by adding 2.5 grams of soy protein isolates into 100 milliliters of distilled water. After 30 minutes of magnetic stirring, 2.5 grams of carvacrol was added to the mixture. The solution was homogenized at 7000 rpm for 10 minutes (ambient temperature) using a T.K. Homomoxer Mark II (Model 2.5), available from PRIMIX Corp. (Japan). The solution was coated onto HYRDOKNIT® substrates (25 cm$^2$) by dipping it into the solution for 1 minute. Thereafter, the coated substrates were removed from the solution beaker and placed in hood to allow the solvent to evaporate off for 3 hours at ambient temperature. The resulting add-on level, after drying, was calculated to be 32% from the following equation:

$$\text{Add-on level (wt \%)} = 100 \times \frac{(\text{wt. of treated substrate} - \text{wt. of untreated substrate})}{\text{wt. of untreated substrate}}$$

The coated substrates were stored for subsequent testing in an open chamber at 40° C. for 1 day, 4 days, and 10 days.

Example 2

A coating solution was initially prepared by adding 2.5 grams of soy protein isolates into 100 milliliters of distilled water. After 30 minutes of magnetic stirring, 2.5 grams of carvacrol was added to the mixture. 8 milliliters of a PDMS silicone emulsion (TM4855) was then added to the mixture. The solution was homogenized at 7000 rpm for 10 minutes (at ambient temperature) using a T.K. Homomoxer Mark II (Model 2.5), available from PRIMIX Corp. (Japan). The solution was coated onto HYRDOKNIT® substrates as described above. The resulting add-on level of the solution, after drying, was calculated to be 28% from the equation above.

The coated substrates were stored for subsequent testing in an open chamber at 40° C. for 1 day, 4 days, and 10 days.

Example 3

Coated substrates were formed as described in Example 2, except that a hydroxyl-terminated PDMS emulsion (TM4856) was employed. The add-on level, after drying, was calculated to be 31% from the equation above. The coated substrates were stored for subsequent testing in a chamber at 40° C. for 1 day, 4 days, and 10 days.

Example 4

A coating solution was initially prepared by adding 2.5 grams of soy protein isolates into 100 milliliters of distilled water. After 30 minutes of magnetic stirring, 2.5 grams of carvacrol was added to the mixture. 1 gram of glycerol was then added to the mixture. The solution was homogenized at 7000 rpm for 10 minutes (at ambident temperature) using a T.K. Homomoxer Mark II (Model 2.5), available from PRIMIX Corp. (Japan). The solution was coated onto HYR-DOKNIT® substrates as described above. The add-on level, after drying, was calculated to be 28% from the equation above. The coated substrates were stored for subsequent testing in a chamber at 40° C. for 1 day, 4 days, and 10 days.

Example 5

A coating solution was initially prepared by dissolving 3 grams of zein and 2 grams of thymol into 100 milliliters of an aqueous alcohol solution (80 vol. % ethanol, 20 vol. % distilled water). The solution was stirred at ambient temperature using a magnetic stirring device until the zein and thymol were fully dissolved. The solution was coated onto a HYRDOKNIT® substrate as described above to an add-on level of 38%, after drying. The coated substrates were stored for subsequent testing in a chamber at 40° C. for 1 day, 4 days, and 10 days.

Test Results

The resulting substrate samples were tested for carvactrol or thymol stability using the test methods described above. The results are set forth below in Table 1.

TABLE 1

Thymol Level After Aging for 1, 4, and 10 Days at 40° C.

| Example | Thymol level (wt. %) | | |
|---|---|---|---|
| | 1 day | 4 days | 10 days |
| C1* | 2.2 | 0.4 | 0.0 |
| C2* | 5.2 | 0.6 | 0.0 |
| 1 | 4.3 | 1.9 | 1.6 |
| 4 | 3.8 | 1.6 | 1.3 |
| 5 | 4.0 | 1.9 | 0.1 |

*Example C1 was prepared by dissolving a 10% carvacrol solution in ethanol and coating the solution onto a HYDRONIT® substrate. Example C2 was prepared by dissolving thymol in aqueous ethanol to form a solution containing 20 wt. % thymol and 80 wt. % ethanol, and coating the solution onto a HYDRONIT® substrate.

As indicated, the essential oil level quickly volatilized from the substrate coated only with essential oil and ethanol (Examples C1 and C2). On the other hand, substrates coated with essential oil/protein solutions retained stability even after 10 days of aging at 40° C.

The substrate samples of Examples 1-5 were also tested for antimicrobial efficacy using the "Zone of Inhibition" test method described above. The results are set forth below in Table 2.

TABLE 2

Zone of Inhibition Area After Aging for 1, 4, and 10 Days

| Exam-ples | Area of inhibition zone (mm) | | | | | |
|---|---|---|---|---|---|---|
| | 1 day | | 4 days | | 10 days | |
| | S. aureus | E. coli | S. aureus | E. coli | S. aureus | E. coli |
| C1 | 0.5 | 0.5 | 0.0 | 0.0 | 0.0 | 0.0 |
| C2 | 0.5 | 0.5 | 0.0 | 0.0 | 0.0 | 0.0 |
| 1 | 2.0 | 3.5 | 0.5 | 1.0 | 0.1 | 1.0 |
| 2 | 1.5 | 1.5 | 1.0 | 0.5 | 0.1 | 0.1 |
| 3 | 1.5 | 1.0 | 0.5 | 0.5 | 0.5 | 0.1 |
| 4 | 1.0 | 1.0 | 0.1 | 0.1 | 0.1 | 0.0 |
| 5 | 2.5 | 3.0 | 1.0 | 2.0 | 0.5 | 0.5 |

As shown, the samples treated with only thymol or carvacrol (C1 and C2)) exhibited no antimicrobial efficacy after 4 days of storage. On the other hand, each of the samples that contained a protein in the solution exhibited antimicrobial activity for both *E. coli* and *S. aureus* after 4 days, and some even after 10 days.

Cup crush testing was also performed to determine the softness of the samples. The results are set forth below in Table 3.

TABLE 3

Cup Crush Results

| Example | Peak Load ($g_f$) |
|---|---|
| HYDROKNIT ® (without coating) | 227 |
| 1 | 686 |
| 2 | 380 |
| 3 | 360 |
| 4 | 590 |

Figure 2:
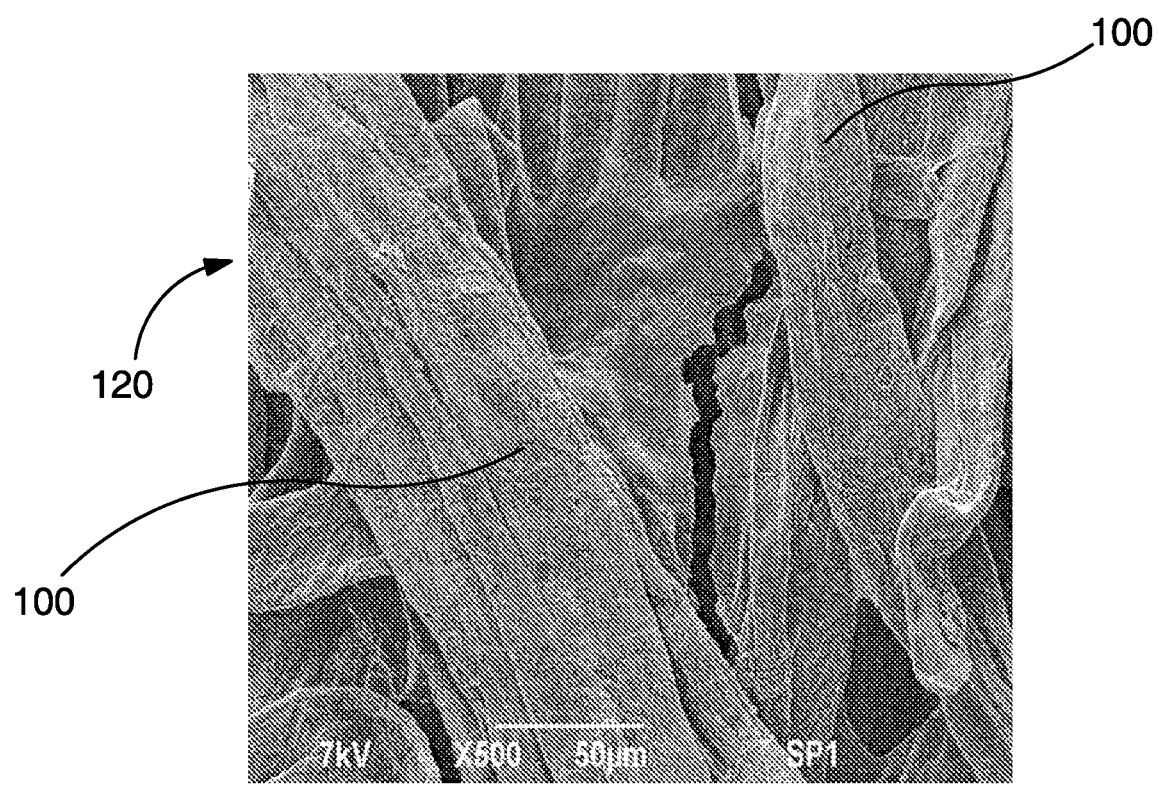
FIG. 2 is an SEM microphotograph of the coated substrate of Example 1, taken at a magnification of 500×.
Figure 3:
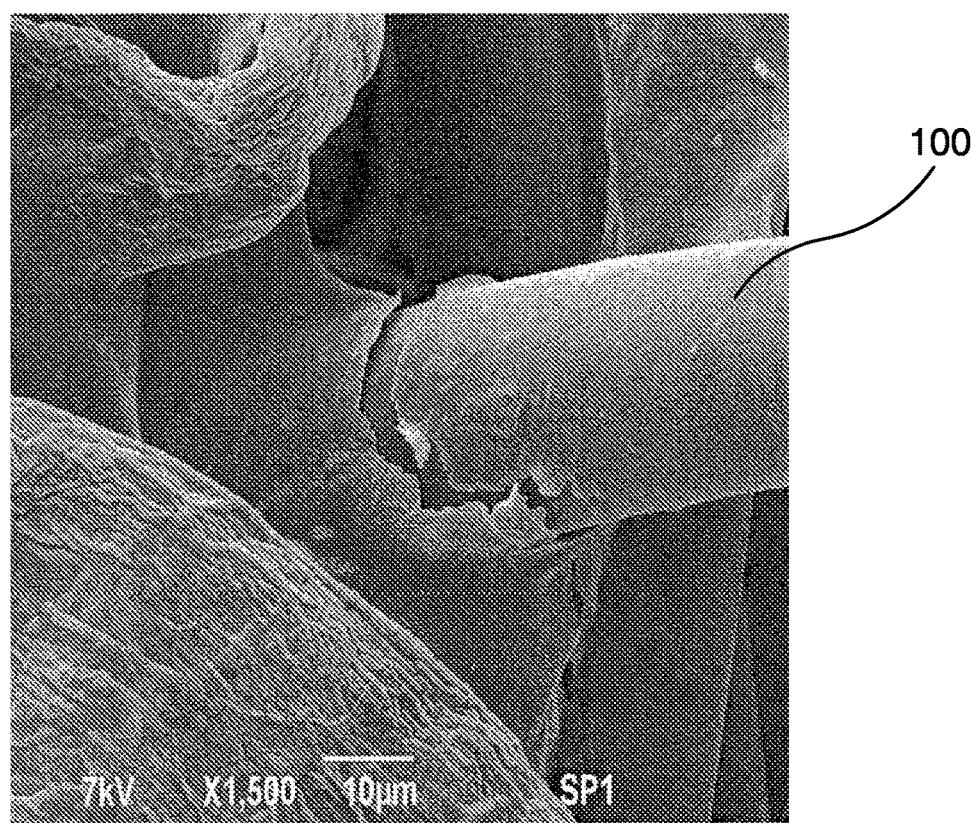
FIG. 3 is an SEM microphotograph of the coated substrate of Example 1, taken at a magnification of 1,500×.
Figure 4:
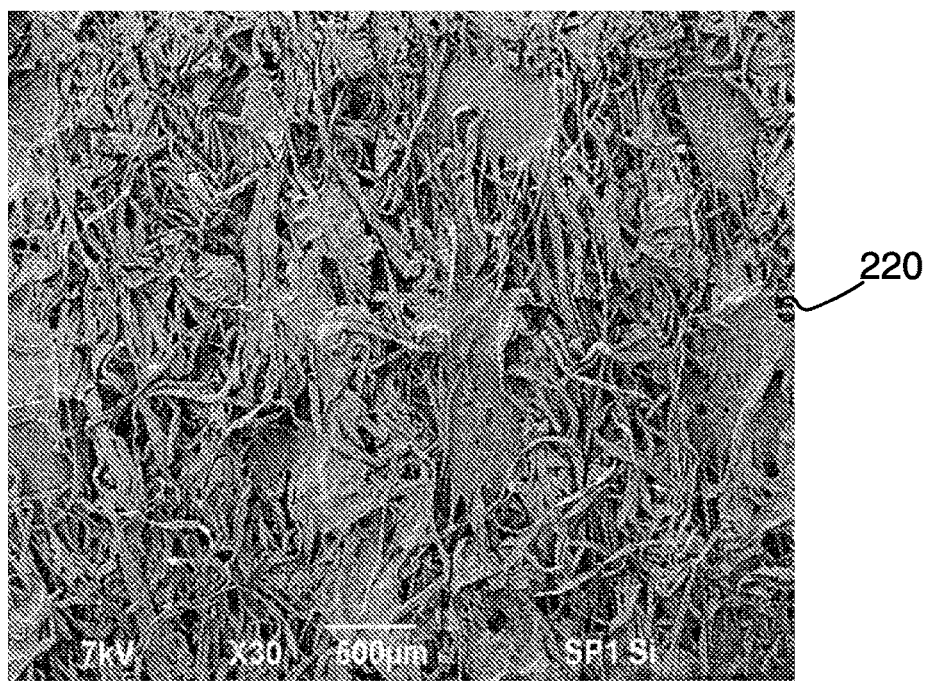
FIG. 4 is an SEM microphotograph of the coated substrate of Example 3, taken at a magnification of 30×.
Figure 5:
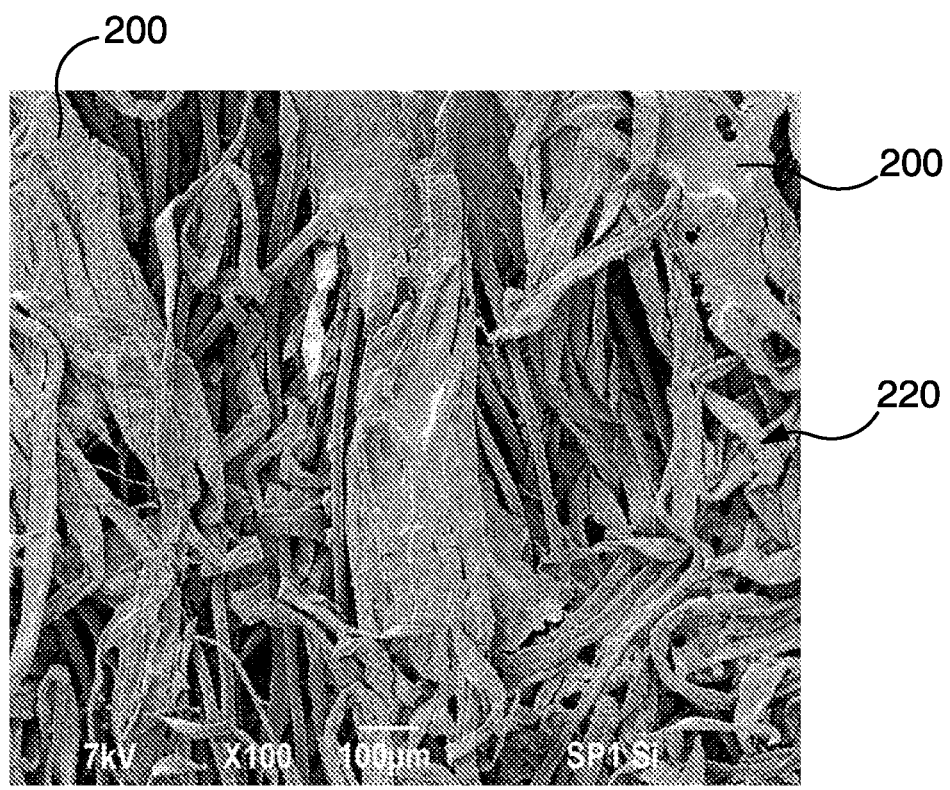
FIG. 5 is an SEM microphotograph of the coated substrate of Example 3, taken at a magnification of 100×.

As indicated, the addition of a silicone emulsion in Example 2 and 3 greatly reduced the stiffness of the coated substrates in comparison to the solutions containing only carvacrol/soy protein (Example 1). However, the addition of glycerol (Example 4), a conventional plasticizer for soy protein, did not noticeably improve softness. To better understand the difference is softness, microphotographs (SEM) were taken the coated substrates of Example 1 (FIGS. 1-3) and Example 3 (FIGS. 4-5). As shown in FIGS. 1-3, the coating 100 that is located on the fibers 120 is substantially continuous in nature. It is believed that this continuous coating resulted in the brittle/stiff feel exhibited by the substrate of Example 1. To the contrary, the coating 200 located on the fibers 220 in FIGS. 4-5 are in the form of irregular patches and thus discontinuous in nature. It is believed that this discontinuous coating resulted in a softer feel exhibited by the substrate of Example 3.

While the invention has been described in detail with respect to the specific embodiments thereof, it will be appreciated that those skilled in the art, upon attaining an understanding of the foregoing, may readily conceive of variations and equivalents to these embodiments. Accordingly, the scope of the present invention should be assessed as that of the appended claims and any equivalents thereto.

What is claimed is:

1. A wipe comprising
   a web that includes a plurality of fibers, wherein the web is coated with an antimicrobial composition comprising a botanical oil,
   a film-forming protein, the botanical oil and the film-forming protein being associated through mixing and/or homogenization such that the film-forming protein is associated with and stabilizes the botanical oil and thereby inhibits premature release of the botanical oil, and
   an organopolysiloxane,
   wherein the composition is configured for delivering the botanical oil to a surface,
   wherein the composition forms a discontinuous coating on at least a portion of the fibers of the web,
   wherein the discontinuous coating forms a pattern that covers from about 5% to about 95% of a surface of the wipe,
   wherein the antimicrobial composition is present on the wipe at a solids add-on level ranging from about 15% to about 70%, and
   wherein the antimicrobial composition has a solvent content of less than about 5 wt. %.

2. The wipe of claim 1, wherein the botanical oil includes a monoterpene phenol.

3. The wipe of claim 2, wherein the monoterpene phenol is thymol, carvacrol, or a mixture thereof.

4. The wipe of claim 1, wherein the botanical oil is derived from a plant oil extract.

5. The wipe of claim 1, wherein the botanical oil is synthesized.

6. The wipe of claim 1, wherein the protein is a plant protein.

7. The wipe of claim 6, wherein the plant protein is zein, corn gluten, wheat gluten, whey protein, soy protein, or a combination thereof.

8. The wipe of claim 6, wherein the plant protein is a soy protein.

9. The wipe of claim 1, wherein the organopolysiloxane is a methylpolysiloxane.

10. The wipe of claim 9, wherein the methylpolysiloxane is polydimethylsiloxane.

11. The wipe of claim 1, wherein the organopolysiloxane contains a hydroxyl functional group, alkoxy functional group, amino functional group, or a combination thereof.

12. The wipe of claim 11, wherein the organopolysiloxane is hydroxy-terminated polydimethylsiloxane.

13. The wipe of claim 1, wherein the antimicrobial composition comprises botanical oils in an amount of from about 0.05 wt. % to about 50 wt. %.

14. The wipe of claim 1, wherein the web is a nonwoven web.

15. The wipe of claim 1, wherein the fibers include absorbent fibers.

16. The wipe of claim 15, wherein the web is a composite of absorbent fibers and synthetic thermoplastic fibers.

17. The wipe of claim 1, wherein the antimicrobial composition further comprises a carbohydrate polymer.

18. The wipe of claim 17, wherein the carbohydrate biopolymer includes a chemically modified starch polymer.

19. The wipe of claim 18, wherein the chemically modified starch polymer is a hydroxyalkyl starch.

20. A method for forming the wipe of claim 1 wipe, the method comprising:
    forming a coating solution that comprises the botanical oil, the film-forming protein, the organopolysiloxane, and a solvent;
    applying the coating solution to the web that includes a plurality of fibers; and
    drying the coating solution to form an antimicrobial coating on the web.

21. The method of claim 20, wherein the monoterpene phenol is thymol, carvacol, or a mixture thereof.

22. The method of claim 20, wherein the protein is a plant protein.

23. The method of claim 20, wherein the coating solution further comprises an organopolysiloxane emulsion.

24. The method of claim 20, wherein the emulsion includes polydimethylsiloxane, modified polydimethylsiloxane, or a combination thereof.

25. The method of claim 20, wherein the antimicrobial coating has a solvent content of less than about 5 wt. %.

26. A method for inhibiting the growth of bacteria on a surface, the method comprising contacting the surface with the wipe of claim 1.

27. The method of claim 26, wherein the composition is in the form of a concentrate.

28. The method of claim 27, wherein prior to contacting the surface with the wipe, water is applied to the concentrate to initiate dispersion of the film-forming protein and release of the botanical oil.

* * * * *